United States Patent [19]
Todtenhaupt et al.

[11] 4,094,638
[45] June 13, 1978

[54] APPARATUS FOR THE CONTINUOUS THERMAL STERILIZATION OF PACKING

[75] Inventors: Erich Todtenhaupt; Wolfgang Müller, both of Schopfheim; Hans Schupper, Zell; Walter Geng, Schopfheim, all of Germany

[73] Assignee: Ekato-Werk, Schopfheim, Germany

[21] Appl. No.: 740,017

[22] Filed: Nov. 8, 1976

[30] Foreign Application Priority Data

Dec. 15, 1975 Germany .............................. 2556467

[51] Int. Cl.² .......................... A61L 1/00; F16J 15/00; F16K 49/00
[52] U.S. Cl. .......................................... 21/61; 21/56; 21/103; 137/241; 277/15; 277/22
[58] Field of Search ............... 21/56, 61, 103; 277/15, 277/22; 259/DIG. 16; 137/241; 195/139, 143; 165/30

[56] References Cited

U.S. PATENT DOCUMENTS

| | | | |
|---|---|---|---|
| 1,795,932 | 3/1931 | Cornell, Jr. | 277/22 X |
| 3,253,882 | 5/1966 | Deackoff | 21/61 X |
| 3,428,413 | 2/1969 | Froelich | 21/61 X |
| 3,909,014 | 9/1975 | Loliger | 137/241 X |

Primary Examiner—Morris O. Wolk
Assistant Examiner—Roger F. Phillips
Attorney, Agent, or Firm—Cushman, Darby & Cushman

[57] ABSTRACT

An apparatus and method for the continuous thermal sterilization of packings on rotating or reciprocating shafts to prevent the entry or exit of microorganisms, wherein the thermal sterilization of the packings results from a flow of steam condensate about the packings, characterized in that at least one part of the steam condensate is circulated in a closed cycle. As a result of circulating in a closed cycle, the required quantity of steam is reduced and energy losses are decreased. The apparatus and method are particularly useful for installations carrying out biological processes.

7 Claims, 1 Drawing Figure

U.S. Patent  June 13, 1978  4,094,638
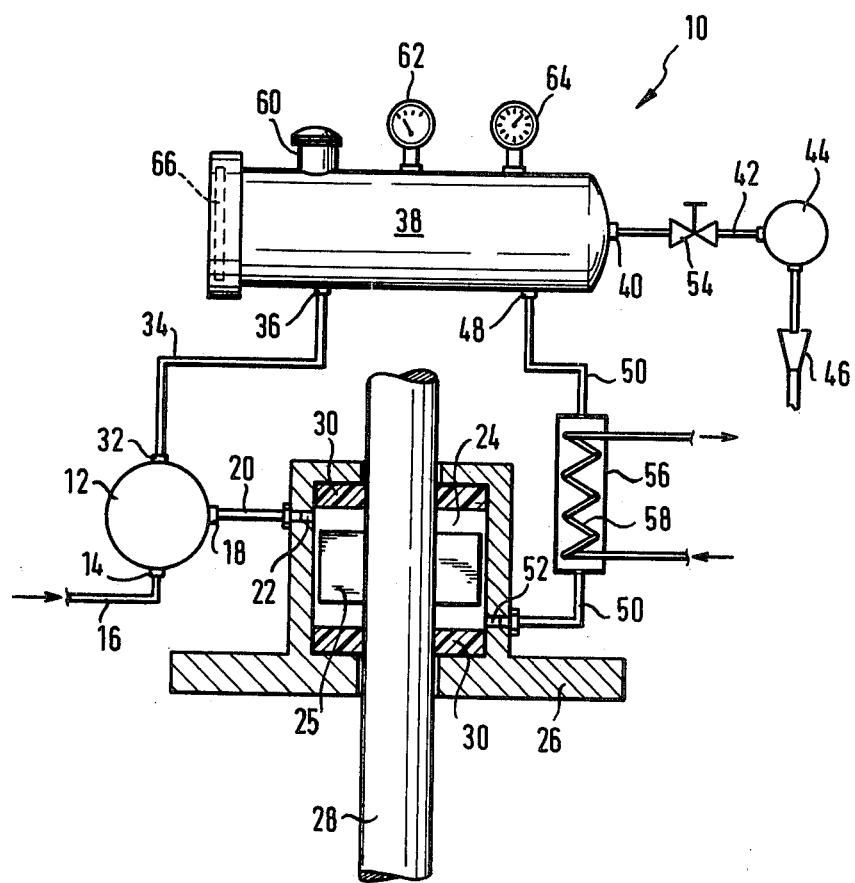

APPARATUS FOR THE CONTINUOUS THERMAL STERILIZATION OF PACKING

BACKGROUND OF THE INVENTION

The invention relates to a process and an apparatus for the continuous thermal sterilization of packings on rotating or reciprocating shafts. Continuous thermal sterilization of packings is required inter alia to avoid the entry or exit of microorganisms from installations used to perform biological processes. The process and apparatus of the invention direct a flow of hot steam condensate through the shaft packing.

Apparatus have been known in the prior art which effect a thermal sterilization of packings with saturated steam. In these prior apparatus, all the elements are connected in a series, from the point of entry of the steam, past the shaft packing, up to the final drain for the steam condensate. These prior apparatus have several disadvantages. For example, they require a very large quantity of steam. Furthermore, they cannot efficiently conduct heat away from the shaft packing because the developing condensate flows only once through the packing on the shaft. As a consequence of this, these prior apparatus are not very efficient and require a very large quantity of steam.

SUMMARY OF THE INVENTION

The present invention provides a process and apparatus for the continuous thermal sterilization of packings on rotating or reciprocating shafts, particularly shafts in biological installations where it is important to avoid the entry or exit of microorganisms, wherein a hot steam condensate flows through the shaft packing.

It is an object of the present invention to provide for such a process and an apparatus which requires relatively small quantities of steam.

Another object of the invention is to provide for such a process and apparatus which can operate more economically.

A further object of the present invention is to provide for such a process and apparatus which avoids the direct contact of steam with the shaft and shaft packing materials.

Yet a further object of the invention is to provide for such a process and apparatus in which the temperature of the hot steam condensate can be adjusted, and maintained below the evaporation temperature of the condensate.

These and other objects of the invention are accomplished by the process and apparatus of the invention in which at least a part of the hot steam condensate flowing through the packing is recirculated in a closed cycle.

BRIEF DESCRIPTION OF THE DRAWING

The FIGURE illustrates an embodiment of the invention schematically. The apparatus consists of two flow paths. One path is a series connected path consisting of steam ejector 12, mixing tank 38 and escape valve 44. Another path, connected in a continuous closed circuit, consists of steam ejector 12, mixing tank 38, packings 30 and sealing chamber 24, and from there back again to the steam ejector.

DETAILED DESCRIPTION OF THE INVENTION

An embodiment by way of example will describe the invention. Attention is directed to the drawing, the only FIGURE of which shows an embodiment of the invention schematically.

The apparatus 10 consists of a steam ejector 12, to which live steam is fed at its inlet 14 via a line 16. Saturated steam is especially preferred. A relief valve, not shown, may be inserted into line 16 before the inlet 14 of steam ejector 12. Such a relief valve prevents the possibility of a return suction developing from a vacuum resulting from a steam failure in supply line 16. The live steam supplied by supply line 16 suitably has a pressure of about +3 bar.

The steam ejector 12 has another inlet 18 which is connected via a line 20 with the outlet 22 of a sealing chamber 24. The sealing chamber 24 is part of a housing 26 in which a shaft 28 is guided and mounted in a manner not shown in detail. The shaft may either exhibit reciprocating motion, or rotating motion, or both. In the sealing chamber 24, packings 30 are disposed which seal the shaft from the area outside of the sealing chamber. These packings are designed especially to avoid the entry or exit of microorganisms from the sealing chamber. In order to sterilize the sealing chamber, a temperature between about 125° to about 130° C is generally required, although in some cases a temperature as high as 135° C is required.

The outlet 32 of the steam ejector 12 is connected via a line 34 with the inlet 36 of a mixing tank 38. The mixing tank 38 is preferably equipped with insertion elements, not shown, for mixing the steam with the water resulting from the condensation of steam (the hot steam condensate), and to prevent water shocks. The mixing tank 38 in addition has a filler cap 60 and a level gauge 66, and may also be equipped with a temperature gauge 62 and a pressure gauge 64.

The mixing tank 38 has two outlets, outlet 40 which is connected via a line 42 with a check valve 54 and a thermally controlled outlet valve 44. The thermally controlled outlet valve 44 is connected with a drain 46 for the steam condensate. The other outlet 48 from the mixing tank 38 is connected via a line 50 with the inlet 52 of the sealing chamber 24. The outlet 40 of the mixing tank 38 is located at a level on the mixing tank 38, which corresponds to about 50% of the total volume of the mixing tank 38. The level gauge 66 has a marking at the level of the outlet 40. The check valve 54 is preferably equipped with an adjusting cone. The thermally controlled outlet valve 44 serves to release the steam condensate from the apparatus, and thereby to control the temperature within the apparatus. The thermally controlled outlet valve 44 may be operated with or without an external energy supply.

The other outlet 48 of the mixing tank 38 is connected via a line 50 with a heat exchanger 56. A cooling liquid, e.g. cooling water, is run through the tubing 58 of the heat exchanger 56. The heat exchanger 56 can be controlled by a temperature sensitive element (not shown), on or near the packing 30. After the heat exchanger 56 the line 50 enters the sealing chamber 24 via inlet 52. Passing through the sealing chamber 24, the cycle begins again.

The apparatus of the present invention operates in the following manner. At the beginning of the operation of the apparatus the mixing tank 38 is filled with distilled water or steam condensate via filling cap 60 up to the marking on level gauge 66 which corresponds to the level of outlet 40. Of course the check valve 54 must be closed while the apparatus is being filled. After the mixing tank 38 is filled with distilled water or steam condensate, the steam inlet 14 of the steam ejector 12 is opened and the steam is fed into the steam ejector via line 16. Steam and steam condensate flow through the mixing tank 38 via line 50 and inlet 52 into the sealing chamber 24 to the packings 30, and from there via the outlet 22 and line 20 back to the steam ejector 12. When the packings 30 have reached a predetermined temperature (e.g. sterilization temperature), the thermally controlled outlet valve 44 closes, maintaining the steam condensate within the apparatus and limiting the entrance of additional steam.

At the beginning of the operation of the apparatus, the packing 30 is slowly heated to the sterilization temperature. This heating should take place during a period of about ten minutes in order to avoid thermal stresses and water shocks. The slow heating of the packing 30 until it reaches sterilization temperatures can be accomplished by either manual or automatic operation of the check valve 54 which is generally kept closed or opened very slowly while the packing is reaching sterilization temperatures. Preferably, the shaft 28 is not in motion while the packing 30 is heated to sterilization.

Whenever the temperature of the steam condensate in the mixing tank 38 drops below the predetermined value (e.g. below the temperature required for sterilization) then the thermally controlled outlet valve 44 opens again and allows steam condensate to leave the apparatus (permitting additional steam to enter the apparatus) until the predetermined temperature is again reached in the mixing tank 38. Thermally controlled outlet valve 44 can be controlled by a temperature sensitive element (not shown) in or in the area of the mixing tank 38.

The apparatus thus described and illustrated in the FIGURE is seen to consist of two flow paths. One flow path, a series connected path, consists of the steam ejector 12, the mixing tank 38, check valve 54, and thermally controlled outlet valve 44. The other flow path is connected in a closed circuit, including steam ejector 12, mixing tank 38, sealing chamber 24 and packings 30, and from there back again to the steam ejector 12.

Although the heat exchanger 56 is preferably disposed between the outlet of the mixing tank 48 and the inlet of the sealing chamber 52, it is not absolutely necessary in the apparatus and process of the present invention. The purpose of the heat exchanger 56 is to reduce the temperature of the hot steam condensate to a point where the heat contained in the packings 30 due to friction with moving shaft 28 can be absorbed and carried off by the steam condensate without excessive evaporation of the hot condensate. Thus the steam condensate flowing through the sealing chamber 24 serves two purposes at the same time. First it sterilizes the packings 30, and secondly it carries off the frictional heat contained within the packings so that this heat is not carried off into the atmosphere through convection. It will be remembered that the apparatus of the present invention is particularly designed for use in biological installations, which may be adversely affected by the introduction of heat from the frictional heat developed in packings 30. It is therefore a particular advantage of the present invention that it affords a method for removal of this heat.

In an embodiment of the invention not illustrated in the FIGURE, it is possible to omit heat exchanger 56. In particular, heat exchanger 56 may be omitted when the apparatus of the present invention is used in an environment which is not adversely affected by a heat flow from the packings 30 to the atmosphere. In such a case, if the heat flow from the packings 30 to the atmosphere is sufficiently great to maintain the temperature of the hot steam condensate at a constant level, rather than becoming progressively hotter, then it is possible to omit heat exchanger 56. Preferably, however, heat exchanger 56 is inserted into line 50. Heat exchanger 56 permits the temperature of the steam condensate flowing into the sealing chamber 24 to be lowered without reducing the pressure in the apparatus. The cooled steam condensate is thus better able to carry off the frictional heat contained in the packings safely and reliably, without excessive evaporation. As has already been mentioned, the heat exchanger 56 can be controlled by means of a temperature sensitive element disposed at or near the packings 30. Although the heat exchanger 56 has been described above as operating with cooled water, it is also possible to provide a heat exchanger 56 with an air-convection cooler. In all cases, the heat exchanger 56 makes it possible to maintain the temperature of the steam condensate in the sealing chamber 24 about the packings 30 lower than the boiling temperature of the steam condensate, thus avoiding excessive evaporation of the steam condensate.

An additional advantage of using the heat exchanger 56 is to prevent any possibility of live steam from flowing into the sealing chamber 24 after leaving the mixing tank 38. The heat exchanger of course would condense any live steam entering line 50, thereby avoiding the possibility of damage to the sealing chamber 24 and the packings 30.

The flow of the steam condensate through the closed cycle of the system is preferably circulated by the kinetic energy of the live steam fed into steam ejector 12 from line 16. The live steam thereby performs two independent functions: it heats the steam condensate to the required sterilization temperature, and its kinetic energy is utilized to circulate the condensate so that no special circulation pumps are required. However, should it be desirable to increase or augment the circulation of the steam condensate through the apparatus, then a circulation pump 25 can be provided in the sealing chamber 24 driven by the shaft 28.

The volume of steam condensate required in the apparatus and process of the invention will of course depend upon the frictional heat developed by the moving shaft 28. In the case, for example, of a rotating shaft 28 125 mm in diameter and rotating at a speed of 100 rpm, about 200 to 300 liters of steam condensate are circulated in the apparatus.

The present invention thus provides for a method of heating the sealing chamber 24 with a steam condensate heated by live steam, the steam condensate being sufficient to sterilize the sealing chamber 24 and packings 30. At the same time, the temperature of the steam condensate is regulated so that it can carry off the frictional heat of the packings without excessive evaporation of the water of the steam condensate.

Thus the invention makes it possible to heat up the steam condensate with a minimum amount of steam, and to maintain the temperature of the steam condensate using the frictional heat of the packings in a constructive manner. The invention thus provides for a wet sterilization of the shaft packings 30 at the point of entry or exit of the shaft into an otherwise closed installation. The temperature of the steam condensate, which must of course be high enough to effect sterilization, is easily adjustable as has been described, and achieves the maximum amount of useful work with the minimum expenditure of energy.

It is understood that various other modifications will be apparent to and can readily be made by those skilled in the art without departing from the scope and spirit of this invention. Accordingly, it is not intended that the scope of the claims appended hereto be limited to the description set forth above, but rather that the claims be construed as encompassing all the features which reside in the present invention, including all features which would be treated as equivalents thereof by those skilled in the art to which the invention pertains.

What is claimed is:

1. An apparatus for the continuous thermal sterilization of packings on rotating and/or reciprocating shafts, comprising:
    a steam ejector means for supplying steam as a source of heat for said thermal sterilization of said packings, said steam ejector means in communication with a mixing tank means,
    a mixing tank means for mixing water with said steam to form hot water for said thermal sterilization of said packings,
    means for supplying water to said mixing tank means in communication with said mixing tank means,
    an outlet means in communication with said mixing tank means at a level effective to maintain at least a portion of said water in said mixing tank means,
    a temperature sensing valve means in communication with said outlet means for measuring the temperature of said water in said mixing tank means and for releasing water from said apparatus when the water temperature in said mixing tank means falls below a pre-determined value, thereby permitting additional steam to enter the apparatus and increase the water temperature,
    a chamber means in communication with said mixing tank means and also in communication with said steam ejector means containing packings for sealing a rotating and/or reciprocating shaft, thereby permitting said hot water to effect thermal sterilization of said packings, and
    a pump means in communication with said chamber means for circulating said hot water in a closed circuit through said steam ejector means, said mixing tank means, said chamber means and again through said steam ejector means.

2. The apparatus of claim 1 including a check valve means in communication with said outlet means for closing said outlet means when said apparatus is initially filled with water.

3. The apparatus of claim 1 including a heat exchanger means in communication with said mixing tank means and said chamber means for reducing the temperature of said hot water circulating in said closed circuit.

4. The apparatus of claim 1 including a relief valve means in communication with said steam ejector means for preventing a return suction developing from a failure in a steam supply.

5. The apparatus of claim 1 including pressure sensing means in communication with said mixing tank means for measuring the pressure in said mixing tank means.

6. The apparatus of claim 1 wherein said outlet means is located at a level with respect to said mixing tank means which corresponds to about 50% of the total volume of said mixing tank means.

7. The apparatus of claim 1 wherein said mixing tank means includes means for mixing steam with water resulting from the condensation of steam.

* * * * *